United States Patent
Vic et al.

(10) Patent No.: US 9,895,299 B2
(45) Date of Patent: Feb. 20, 2018

(54) PROCESS FOR BLEACHING OR DYEING KERATIN FIBRES USING AN OXIDIZING COMPOSITION AND UV-VISIBLE RADIATION

(71) Applicant: L'OREAL, Paris (FR)

(72) Inventors: Gabin Vic, Semoy (FR); Frédéric Woodland, Gagny (FR); Fabrice Osolin, Franconville (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/306,778

(22) PCT Filed: Apr. 29, 2015

(86) PCT No.: PCT/EP2015/059312
§ 371 (c)(1),
(2) Date: Oct. 26, 2016

(87) PCT Pub. No.: WO2015/165949
PCT Pub. Date: Nov. 5, 2015

(65) Prior Publication Data
US 2017/0042776 A1    Feb. 16, 2017

(30) Foreign Application Priority Data

Apr. 30, 2014 (FR) ..................................... 14 53963

(51) Int. Cl.
| | | |
|---|---|---|
| *A61Q 5/10* | (2006.01) | |
| *A61K 8/22* | (2006.01) | |
| *A61Q 5/08* | (2006.01) | |
| *A61K 8/19* | (2006.01) | |
| *A61K 8/23* | (2006.01) | |
| *A45D 19/00* | (2006.01) | |
| *A61K 8/34* | (2006.01) | |
| *A61K 8/41* | (2006.01) | |

(52) U.S. Cl.
CPC ................ *A61K 8/22* (2013.01); *A45D 19/00* (2013.01); *A61K 8/19* (2013.01); *A61K 8/23* (2013.01); *A61K 8/345* (2013.01); *A61K 8/411* (2013.01); *A61Q 5/08* (2013.01); *A61Q 5/10* (2013.01); *A45D 2019/0075* (2013.01); *A61K 2800/4324* (2013.01); *A61K 2800/81* (2013.01)

(58) Field of Classification Search
CPC ... A61Q 5/08; A61Q 5/10; A61K 8/19; A61K 8/22; A61K 8/345; A61K 8/411; A61K 2800/81; A61K 2800/4324
See application file for complete search history.

(56) References Cited

U.S. PATENT DOCUMENTS

| | | | |
|---|---|---|---|
| 4,003,699 A | 1/1977 | Rose et al. | |
| RE30,199 E | 1/1980 | Rose et al. | |
| 4,792,341 A | 12/1988 | Kozikowski et al. | |
| 5,061,289 A | 10/1991 | Clausen et al. | |
| 5,246,019 A | 9/1993 | Godfrey et al. | |
| 5,303,722 A | 4/1994 | Godfrey et al. | |
| 5,380,340 A | 1/1995 | Neunhoeffer et al. | |
| 5,534,267 A | 7/1996 | Neunhoeffer et al. | |
| 5,663,366 A | 9/1997 | Neunhoeffer et al. | |
| 5,679,113 A | 10/1997 | Caisey et al. | |
| 5,713,961 A | 2/1998 | Caisey et al. | |
| 5,725,600 A | 3/1998 | Caisey et al. | |
| 5,766,576 A | 6/1998 | Löwe et al. | |
| 6,099,592 A | 8/2000 | Vidal et al. | |
| 6,284,003 B1 | 9/2001 | Rose et al. | |
| 6,338,741 B1 | 1/2002 | Vidal et al. | |
| 6,645,258 B2 | 11/2003 | Vidal et al. | |
| 6,730,789 B1 | 5/2004 | Birault et al. | |
| 2002/0050013 A1 | 5/2002 | Vidal et al. | |
| 2003/0019051 A9 | 1/2003 | Vidal et al. | |
| 2007/0167936 A1* | 7/2007 | Samain ................ A45D 19/00 606/9 |
| 2011/0017227 A1 | 1/2011 | Samain | |

FOREIGN PATENT DOCUMENTS

| | | |
|---|---|---|
| DE | 2359399 A1 | 6/1975 |
| DE | 3843892 A1 | 6/1990 |
| DE | 4133957 A1 | 4/1993 |
| DE | 19543988 A1 | 5/1997 |
| DE | 19942074 A1 | 3/2001 |
| DE | 102005052139 A1 | 5/2007 |
| EP | 0770375 A1 | 5/1997 |
| FR | 2719472 A1 | 11/1995 |
| FR | 2733749 A1 | 11/1996 |
| FR | 2801308 A1 | 5/2001 |
| FR | 2886136 A1 | 12/2006 |
| FR | 2924597 A1 | 6/2009 |
| GB | 1026978 A | 4/1966 |
| GB | 1153196 A | 5/1969 |
| JP | 02-019576 A | 1/1990 |
| JP | 05-163124 A | 6/1993 |
| WO | 91/06279 A2 | 5/1991 |
| WO | 94/08969 A1 | 4/1994 |
| WO | 94/08970 A1 | 4/1994 |
| WO | 96/15765 A1 | 5/1996 |
| WO | 2007/048473 A1 | 5/2007 |

OTHER PUBLICATIONS

International Search Report for PCT/EP2015/059312, dated Jul. 23, 2015.

* cited by examiner

*Primary Examiner* — Eisa Elhilo
(74) *Attorney, Agent, or Firm* — The Marbury Law Group, PLLC

(57) ABSTRACT

The present invention relates to a process for bleaching or dyeing keratin fibers, in particular human keratin fibers such as the hair, comprising a step of application, to said fibers, of a composition (A) containing one or more chemical oxidizing agents and a step of irradiation of said fibers by means of UV-visible radiation having a wavelength ranging from 200 to 800 nm and a fluence ranging from 1 to 5000 $J/cm^2$, after application of said composition (A); when the process is a process for dyeing keratin fibers, then one or more oxidation dyes is or are also used.

15 Claims, No Drawings

PROCESS FOR BLEACHING OR DYEING KERATIN FIBRES USING AN OXIDIZING COMPOSITION AND UV-VISIBLE RADIATION

CROSS REFERENCE TO RELATED APPLICATIONS

This is a national stage application of PCT/EP2015/059312, filed internationally on Apr. 29, 2015, which claims priority to French Application No. 1453963, filed on Apr. 30, 2014, both of which are incorporated by reference herein in their entireties.

The present invention relates to a process for bleaching or dyeing keratin fibres, in particular human keratin fibres such as the hair, comprising a step of application, to said fibres, of a composition containing one or more chemical oxidizing agents followed by a step of irradiation of said fibres by means of UV-visible radiation having a wavelength ranging from 200 to 800 nm and a fluence ranging from 1 to 5000 J/cm$^2$, after application of said composition, it being understood that, when the process according to the invention is a process for dyeing keratin fibres, one or more oxidation dyes is or are also used.

The invention relates to the technical field of bleaching and dyeing keratin fibres, in particular to the field of hair bleaching and dyeing.

The bleaching or lightening of keratin fibres, in particular human keratin fibres such as the hair, is performed by oxidation of the "melanin" pigment resulting in the dissolution and partial or total removal of this pigment.

Processes for lightening or bleaching human keratin fibres generally consist in applying an aqueous composition comprising at least one oxidizing agent, under alkaline pH conditions in the vast majority of cases. The role of this oxidizing agent is in particular to degrade the melanin of the keratin fibres, which, depending on the nature of the oxidizing agent present, leads to more or less pronounced lightening of the fibres. Thus, for relatively weak lightening, the oxidizing agent is generally hydrogen peroxide. When more pronounced lightening is desired, peroxygenated salts, for instance persulfates, are usually used in the presence of hydrogen peroxide.

Moreover, it is known practice to dye keratin fibres, in particular human keratin fibres such as the hair, to obtain "permanent" colourings with dye compositions containing oxidation dye precursors, which are generally known as oxidation bases, such as ortho- or para-phenylenediamines, ortho- or para-aminophenols, or heterocyclic compounds such as pyrazoles, pyrazolinones or pyrazolo-pyridines. These oxidation bases are colourless or weakly coloured compounds, which, when combined with oxidizing products, may give rise to coloured compounds via a process of oxidative condensation.

It is also known that the shades obtained with these oxidation bases may be varied by combining them with colouring couplers or modifiers, the latter being chosen in particular from aromatic meta-diamines, meta-aminophenols, meta-diphenols and certain heterocyclic compounds such as indole or pyridine compounds. The variety of molecules used as oxidation bases and couplers allows a wide range of colours to be obtained.

Standard oxidation dyeing processes consist generally in applying to keratin fibres a dye composition comprising oxidation bases or a mixture of oxidation bases and couplers with hydrogen peroxide ($H_2O_2$ or aqueous hydrogen peroxide solution), as oxidizing agent, in leaving it to diffuse, and then in rinsing said fibres. The colourings resulting therefrom are generally permanent, strong and resistant to external agents, in particular to light, bad weather, washing, perspiration and rubbing.

The lightening and dyeing processes described in the prior art usually have the drawback of comprising steps of which the implementation times prove to be quite long. For example, a lightening process may comprise a step of leaving in the oxidizing composition which may reach up to 50 minutes, to which it is generally necessary to add the required time linked to the application of said composition. In other words, the application times and the leave-in times for the compositions used during such lightening and dyeing processes prove to be quite considerable, which can make their use tiresome for the user and/or the hairstyler.

Such lightening and dyeing processes also have the disadvantage of using compositions which have quite high concentrations of active substances, such as of alkaline agents, of oxidizing agents and/or of dyes, which can make these processes expensive.

Furthermore, standard lightening processes have the drawback of modifying the natural shade of the keratin fibres during bleaching thereof, which usually results in the appearance of an unattractive orangey background. For this reason, it is sought to develop lightening processes which are friendlier to the natural shades of keratin fibres.

Standard lightening processes also have the disadvantage of harming the integrity of keratin fibres, which can result in unfavourable cosmetic properties.

Moreover, bleaching processes which use a light source are already known from the prior art.

Indeed, U.S. Pat. No. 4,792,341 describes a bleaching process comprising a step of irradiation carried out by means of a laser or a flash lamp.

Patent application WO 91/06279 describes, for its part, a bleaching process by photochemistry using a composition containing from 0.5% to 5% by weight of a photosensitizer and a composition which can release a hydrogen radical.

Finally, patent application WO 2007/048473 describes a dyeing or bleaching process using a step of irradiation by means of UV radiation having a wavelength ranging from 200 to 600 nm or with particular irradiation devices.

These documents do not describe effective dyeing or bleaching processes which use a step of irradiation by means of UV-visible radiation having a particular fluence range.

There is therefore a real need to develop processes for bleaching or dyeing keratin fibres, in particular human keratin fibres such as the hair, which do not have the drawbacks mentioned above, i.e. which are faster to carry out and which use compositions in which the concentrations of active agents, in particular of oxidizing agents and/or of oxidation dyes or else of alkaline agents, are low while being capable of being kind to the natural shades and the integrity of the keratin fibres.

This aim is achieved by the present invention, of which a subject is in particular a process for bleaching or dyeing keratin fibres, in particular human keratin fibres such as the hair, comprising:

(i) a step of application, to said fibres, of a composition containing one or more chemical oxidizing agents, and (ii) a step of irradiation of said fibres by means of UV-visible radiation having a wavelength ranging from 200 to 800 nm and a fluence ranging from 1 to 5000 J/cm$^2$, after application of said composition, it being understood that, when the process according to the invention is a process for dyeing keratin fibres, then said process uses one or more oxidation dyes.

In other words, the process according to the invention uses successively a step of application of a composition containing one or more chemical oxidizing agents and a step of irradiation of the fibres as previously described.

The bleaching or dyeing process according to the invention makes it possible, respectively, to lighten or to dye the fibres more rapidly than standard processes by virtue of the implementation of an irradiation step as previously described. In other words, the irradiation step makes it possible to advantageously reduce the leave-in time required for the oxidizing composition to efficiently lighten or dye the keratin fibres. In particular, such a leave-in time may have a duration of less than 60 minutes, which corresponds to the fibre irradiation time. It results therefrom that the process according to the invention makes it possible to reduce the keratin fibre treatment time, thereby making it easier to implement.

Moreover, it is observed that the process according to the invention can result in a strong bleaching of more than 5 tone levels (TLs) in less than 15 minutes.

Furthermore, the process according to the invention makes it possible to reduce the amounts of active agents of the invention, such as the oxidizing agents and/or the dyes and/or the basifying agents.

Advantageously, the irradiation step is carried out by means of a light-emitting source which makes the process according to the invention more efficient.

In particular, the light-emitting source makes it possible to produce more rapidly a lightening equivalent to that obtained with a non-light-emitting light source.

The use of the light-emitting source is advantageous since this source is not very bulky, and has a low energy consumption, a higher irradiance and a longer lifetime than a filament or arc lamp.

Furthermore, the light-emitting source makes it possible to give off little heat towards the irradiation zone.

Moreover, when the process according to the invention is a dyeing process, the latter leads in particular to powerful, chromatic and/or sparingly selective colourings, i.e. colourings that are uniform along the fibre.

In parallel, when the process according to the invention is a bleaching process, the latter leads to improved lightening performance levels while being capable of being kinder to the natural shade and the integrity of the keratin fibres than the lightening processes of the prior art. Indeed, it is noted that the keratin fibres treated with the lightening process according to the invention do not exhibit a lightening background that is as orangey as the fibres treated with the lightening processes of the prior art.

In other words, the lightening process according to the invention makes it possible to produce tints or shades that are more natural and aesthetic.

The present invention also relates to a process for bleaching or dyeing keratin fibres, in particular human keratin fibres such as the hair, comprising:

(i) a step of application, to said fibres, of a composition comprising one or more chemical oxidizing agents, (ii) a step of irradiation of the keratin fibres by means of one or more diodes after application of said composition, when the process is a process for dyeing keratin fibres, then said process also uses one or more oxidation dyes.

Other characteristics and advantages of the invention will emerge more clearly on reading the description and the examples that follow.

In the text hereinbelow, and unless otherwise indicated, the limits of a range of values are included within that range.

The human keratin fibres treated by means of the process according to the invention are preferably the hair.

The expression "at least one" is equivalent to the expression "one or more".

For the purposes of the present invention, the term "chemical oxidizing agent" is intended to mean an oxidizing agent other than atmospheric oxygen.

The chemical oxidizing agent(s) may be chosen from hydrogen peroxide, urea peroxide, alkali metal bromates or ferricyanides, peroxygenated salts, for instance alkali metal or alkaline-earth metal persulfates, perborates and percarbonates, and also peracids and precursors thereof.

Preferably, the chemical oxidizing agent(s) are chosen from hydrogen peroxide and peroxygenated salts, in particular alkali metal or alkaline-earth metal persulfates, such as potassium persulfate, sodium persulfate, ammonium persulfate, and also mixtures thereof.

More preferentially, the oxidizing agent is hydrogen peroxide.

The oxidizing agent can be present in the oxidizing composition in a content ranging from 1% to 40% by weight, more particularly from 1% to 20% by weight and better still from 2% to 10% by weight, relative to the total weight of the oxidizing composition.

As previously indicated, in the case of the implementation of a dyeing process, the process also uses one or more oxidation dyes.

In other words, one or more oxidation dyes are used during said process.

The oxidation dyes may be chosen from one or more oxidation bases, optionally in combination with one or more couplers. Preferably, the oxidation dyes comprise at least one oxidation base and at least one coupler.

By way of example, the oxidation bases are chosen from para-phenylenediamines, bis(phenyl)alkylenediamines, para-aminophenols, ortho-aminophenols and heterocyclic bases, and the addition salts thereof.

Among the para-phenylenediamines, examples that may be mentioned include para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-methoxymethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, 3-hydroxy-1-(4'-aminophenyl)pyrrolidine, and the addition salts thereof with an acid.

Among the para-phenylenediamines mentioned above, para-phenylenediamine, para-tolylenediamine, 2-methoxymethyl-para-phenylenediamine, 2-isopropylpara-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, are particularly preferred.

Among the bis(phenyl)alkylenediamines, examples that may be mentioned include N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,6-dioxaoctane and the addition salts thereof.

Among the para-aminophenols, examples that may be mentioned include para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols, examples that may be mentioned include 2-aminophenol, 2-amino-5-methylphenol, 2-amino-6-methylphenol, 5-acetamido-2-aminophenol and the addition salts thereof.

Among the heterocyclic bases, examples that may be mentioned include pyridine derivatives, pyrimidine derivatives and pyrazole derivatives.

Among the pyridine derivatives, mention may be made of the compounds described, for example, in patents GB 1 026 978 and GB 1 153 196, such as 2,5-diaminopyridine, 2-(4-methoxyphenyl)amino-3-aminopyridine and 3,4-diaminopyridine, and the addition salts thereof.

Other pyridine oxidation bases that are useful in the present invention are the 3-aminopyrazolo[1,5-a]pyridine oxidation bases or the addition salts thereof, described, for example, in patent application FR 2 801 308. Examples that may be mentioned include 2-(2-hydroxyethoxy)-3-aminopyrazolo[1,5-a]pyridine, pyrazolo[1,5-a]pyrid-3-ylamine, 2-acetylaminopyrazolo[1,5-a]pyrid-3-ylamine, 2-(morpholin-4-yl)pyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl) ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-(morpholin-4-yl)pyrazolo[1,5-a]pyrid-3-ylamine, pyrazolo[1,5-a]pyridine-3,5-diamine, 5-(morpholin-4-yl)pyrazolo[1,5-a]pyrid-3-ylamine, 2-[(3-aminopyrazolo[1,5-a]pyrid-5-yl)(2-hydroxyethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol and 3-aminopyrazolo[1,5-a]pyridin-7-ol, and the addition salts thereof.

Among the pyrimidine derivatives, mention may be made of the compounds described, for example, in patents DE 2359399, JP 88-169571, JP 05-63124 and EP 0 770 375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and the addition salts thereof, and the tautomeric forms thereof, when a tautomeric equilibrium exists.

Among the pyrazole derivatives that may be mentioned are the compounds described in patents DE 3843892, DE 4133957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-amino ethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethypamino-1-methylpyrazole, and the addition salts thereof. Use may also be made of 4,5-diamino-1-(β-methoxyethyl) pyrazole.

Use will preferably be made of a 4,5-diaminopyrazole and even more preferentially of 4,5-diamino-1-(β-hydroxyethyl)pyrazole and/or a salt thereof.

Pyrazole derivatives that may also be mentioned include diamino-N,N-dihydropyrazolopyrazolones and in particular those described in patent application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylaminopyrrolidin-1-yl)-1,2-diethyl-1,2-dihydropyrazol-3-one or 2,3-diamino-6-hydroxy-6,7-dihydro-1H,5H-pyrazolo[1,2-a]pyrazol-1-one.

Use will preferably be made of 2,3-diamino-6,7-dihydro-1H,5H-pyrazolo[1,2-a]pyrazol-1-one and/or a salt thereof.

Heterocyclic bases that will preferentially be used include 4,5-diamino-1-(β-hydroxyethyl)pyrazole and/or 2,3-diamino-6,7-dihydro-1H,5H-pyrazolo[1,2-a]pyrazol-1-one and/or a salt thereof.

Preferably, the oxidation bases are chosen from para-phenylenediamine, 2-methoxymethyl-para-phenylenediamine, 2-β-hydroxyethyl-para-phenylenediamine, N,N-bis(β-hydroxyethyl)-para-phenylenediamine, 1-methyl-2,5-diaminobenzene, para-aminophenol, 1-hydroxyethyl-4,5-diaminopyrazole sulfate, 2,3-diaminodihydroxypyrazo lone dimethosulfonate, 2-(2-hydroxyethoxy)-3-aminopyrazolo[1,5-a]pyridine, the addition salts thereof and mixtures thereof.

The coupler(s) are advantageously chosen from those conventionally used for the dyeing of keratin fibres.

Among these couplers, mention may be made in particular of meta-phenylenediamines, meta-aminophenols, meta-diphenols, naphthalene-based couplers and heterocyclic couplers, and also the addition salts thereof.

Examples that may be mentioned include 2-methyl-5-aminophenol, 5-amino-6-chloro-2-methylphenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureido aniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, the addition salts thereof with an acid, and mixtures thereof.

In general, the addition salts of the oxidation bases and of the couplers that may be used in the context of the invention are in particular chosen from addition salts with an acid such as hydrochlorides, hydrobromides, sulfates, citrates, succinates, tartrates, lactates, tosylates, benzenesulfonates, phosphates and acetates.

Preferably, the coupler(s) are chosen from resorcinol, 2-methylresorcinol, 5-amino-6-chloro-2-methylphenol, 2-amino-4-(β-hydroxyethylamino)-1-methoxybenzene, 5-N-(β-hydroxyethypamino-2-methylphenol, 2-methyl-5-aminophenol, 1-β-hydroxyethyloxy-2,4-diaminobenzene dihydrochloride and 3-aminophenol, the addition salts thereof and mixtures thereof.

The oxidation base(s) and optionally the coupler(s) may advantageously represent from 0.001% to 30% by weight, preferably from 0.1% to 20% by weight and better still from 0.2% to 10% by weight relative to the total weight of the oxidizing composition.

Preferably, the oxidizing composition also comprises one or more basifying agents. The basifying agent(s) may be inorganic or organic or hybrid.

The inorganic basifying agent(s) are preferably chosen from aqueous ammonia, alkali metal carbonates or bicarbonates such as sodium carbonate, potassium carbonate, sodium bicarbonate or potassium bicarbonate, sodium hydroxide or potassium hydroxide, or mixtures thereof.

The organic basifying agent(s) are preferably chosen from organic amines with a $pK_b$ at 25° C. of less than 12, preferably less than 10 and even more advantageously less than 6. It should be noted that it is the $pK_b$ corresponding to the function of highest basicity. In addition, the organic amines do not comprise any alkyl or alkenyl fatty chain comprising more than ten carbon atoms.

The organic basifying agent(s) are chosen, for example, from alkanolamines, oxyethylenated and/or oxypropylenated ethylenediamines, amino acids and the compounds of formula (AII) below:

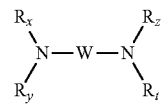

(AII)

in which formula (AII) W is a divalent $C_1$-$C_6$ alkylene radical optionally substituted with one or more hydroxyl groups or a $C_1$-$C_6$ alkyl radical, and/or optionally interrupted with one or more heteroatoms such as O, or $NR_u$; $R_x$, $R_y$, $R_z$, $R_t$ and $R_u$, which may be identical or different, represent a hydrogen atom or a $C_1$-$C_6$ alkyl, $C_1$-$C_6$ hydroxyalkyl or $C_1$-$C_6$ aminoalkyl radical.

Examples of amines of formula (AII) that may be mentioned include 1,3-diaminopropane, 1,3-diamino-2-propanol, spermine and spermidine.

The term "alkanolamine" is intended to mean an organic amine comprising a primary, secondary or tertiary amine function, and one or more linear or branched $C_1$-$C_8$ alkyl groups bearing one or more hydroxyl radicals.

The organic amines chosen from alkanolamines such as monoalkanolamines, dialkanolamines or trialkanolamines comprising one to three identical or different $C_1$-$C_4$ hydroxyalkyl radicals are in particular suitable for carrying out the invention.

Among the compounds of this type, mention may be made of monoethanolamine (MEA), diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethylamino)methane.

More particularly, the amino acids that may be used are of natural or synthetic origin, in their L, D or racemic form, and comprise at least one acid function more particularly chosen from carboxylic acid, sulfonic acid, phosphonic acid and phosphoric acid functions. The amino acids may be in neutral or ionic form.

As amino acids that can be used in the present invention, mention may be made in particular of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine.

Advantageously, the amino acids are basic amino acids comprising an additional amine function optionally included in a ring or in a ureido function.

Such basic amino acids are preferably chosen from those corresponding to formula (AIII) below:

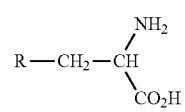

(AIII)

in which formula (AIII), R represents a group chosen from:

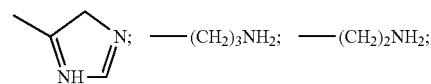

-continued

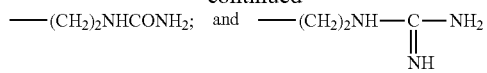

The compounds corresponding to formula (AIII) are histidine, lysine, arginine, ornithine and citrulline.

The organic amine may also be chosen from organic amines of heterocyclic type. Besides histidine that has already been mentioned in the amino acids, mention may in particular be made of pyridine, piperidine, imidazole, triazole, tetrazole and benzimidazole.

The organic amine may also be chosen from amino acid dipeptides. As amino acid dipeptides that may be used in the present invention, mention may in particular be made of carnosine, anserine and balenine.

The organic amine may also be chosen from compounds comprising a guanidine function. As organic amines of this type that may be used in the present invention, besides arginine, which has already been mentioned as an amino acid, mention may be made in particular of creatine, creatinine, 1,1-dimethylguanidine, 1,1-diethylguanidine, glycocyamine, metformin, agmatine, N-amidinoalanine, 3-guanidinopropionic acid, 4-guanidinobutyric acid and 2-([amino (imino)methyl]amino)ethane-1-sulfonic acid.

Hybrid compounds that may be mentioned include the salts of the amines mentioned previously with acids such as carbonic acid or hydrochloric acid.

Guanidine carbonate or monoethanolamine hydrochloride may be used in particular.

Preferably, the basifying agent(s) present in the oxidizing composition are chosen from aqueous ammonia and alkanolamines.

Even more preferentially, the basifying agent is aqueous ammonia or monoethanolamine.

Advantageously, the composition according to the invention has a content of basifying agent(s) ranging from 0.1% to 20% by weight and preferably from 1% to 10% by weight relative to the weight of the composition.

The oxidizing composition is preferably aqueous.

In particular, the oxidizing composition is an aqueous composition comprising one or more chemical oxidizing agents and one or more basifying agents.

The composition may optionally comprise one or more solvents.

Examples of organic solvents that may be mentioned include linear or branched $C_2$-$C_4$ alkanols, such as ethanol and isopropanol; glycerol; polyols and polyol ethers, such as 2-butoxyethanol, propylene glycol, dipropylene glycol, propylene glycol monomethyl ether, diethylene glycol monoethyl ether and monomethyl ether, and also aromatic alcohols, for instance benzyl alcohol or phenoxyethanol, and mixtures thereof.

The solvent(s), if they are present, represent a content usually ranging from 1% to 40% by weight and preferably ranging from 5% to 30% by weight relative to the weight of the cosmetic composition.

The oxidizing composition may also comprise one or more adjuvants conventionally used in compositions for bleaching or dyeing fibres, such as anionic, cationic, non-ionic, amphoteric or zwitterionic polymers or mixtures thereof; inorganic thickeners, and in particular fillers such as clays or talc; organic thickeners with, in particular, anionic, cationic, non-ionic and amphoteric polymeric associative thickeners other than the polymers previously mentioned; anionic, non-ionic, cationic and/or amphoteric surfactants, antioxidants; penetrants; sequestrants; fragrances; dispersants; film-forming agents; ceramides; preserving agents; opacifiers.

The oxidizing composition may be in various forms, for instance a solution, an emulsion or a gel.

Advantageously, the oxidizing composition does not exhibit a chemical absorption peak in the range of wavelengths used for the irradiation step so as to limit the heating of the oxidizing composition during said irradiation.

The oxidizing composition can be obtained by mixing at least two compositions.

In particular, the oxidizing composition can result from the mixing of a composition containing one or more chemical oxidizing agents and a composition containing one or more alkaline agents.

More particularly, the oxidizing composition can result from the mixing of a composition containing one or more chemical oxidizing agents and a composition containing one or more alkaline agents and/or one or more oxidation dyes.

Indeed, when the process according to the invention is a dyeing process, then the oxidizing composition can result from the mixing of a composition containing one or more chemical oxidizing agents and a composition containing one or more alkaline agents and one or more oxidation dyes.

As indicated hereinabove, the invention also relates to a process for bleaching or dyeing keratin fibres, in particular human keratin fibres such as the hair, comprising:

(i) a step of application, to said fibres, of a composition comprising one or more chemical oxidizing agents, (ii) a step of irradiation of the keratin fibres by means of one or more diodes after application of said composition, when the process is a process for dyeing keratin fibres, then one or more oxidation dyes is or are also used.

As previously indicated, the process according to the invention comprises a step of irradiation of the keratin fibres by means of UV-visible radiation having a wavelength ranging from 200 to 800 nm and a fluence ranging from 1 to 5000 J/cm$^2$, after application of said composition, Preferably, 90% of the energy of the radiation emitted by the irradiation source is between 200 and 800 nm. More preferentially, 95% of the energy of the radiation emitted by the irradiation source is between 200 and 800 nm.

In one preferred variant of the invention, the light source emits "monochromatic" radiation, i.e. radiation centred on a given wavelength with a very low dispersion of the energy emitted outside a range of ±10 nanometers relative to said wavelength.

Preferably, the UV-visible radiation has a wavelength ranging from 300 to 600 nm and particularly ranging from 350 to 450 nm.

More particularly, the UV-visible radiation has a wavelength of 365 nm, 385 nm or 405 nm (±10 nanometers).

Preferably, the fluence of the UV-visible radiation ranges from 50 to 2000 J/cm$^2$, in particular from 100 to 2000 J/cm$^2$, particularly from 200 to 1000 J/cm$^2$.

Advantageously, the irradiation step of the process according to the invention is carried out using one or more light sources, preferably one or more light-emitting sources.

More advantageously, the UV-visible radiation is emitted by one or more light-emitting sources made up of one or more light-emitting elements such as light-emitting diodes (LEDs) or organic light-emitting diodes (OLEDs).

The light-emitting source can be chosen from light-emitting diodes (LEDs) or organic light-emitting diodes (OLEDs).

In other words, the irradiation step is carried out by means of one or more light-emitting sources, thereby making it possible to efficiently reduce the treatment time of the process.

Preferably, the irradiation source may be composed of one or more light-emitting diodes.

The diodes further have the advantage of being easier to miniaturize and more energetic. The diodes also make it possible to reduce the irradiation time for a given fluence.

In particular, the irradiation source used in the process according to the invention is a UVA LED bank, Lightnincure LC-L5 365 nm model, sold by Hamamatsu.

The UV-visible radiation may be continuous or may be pulsed at a pulse frequency ranging from 0.001 to 1000 Hz and preferably ranging from 0.01 to 100 Hz.

In one variant of the invention, the irradiance of the radiation emitted by the source(s) is greater than or equal to 50 mWatt/$cm^2$ on the substrate treated.

Preferably, the keratin fibres, once treated with the oxidizing composition, are irradiated for a period of less than 60 minutes, especially for a period of less than 50 minutes, in particular for a period of less than 20 minutes, and more preferentially for a period ranging from 1 to 15 minutes.

Preferably, the process according to the invention also comprises a step of rinsing out the oxidizing composition after the irradiation step.

According to one variant of the invention, the oxidizing composition is applied to a part of the surface of the keratin fibres, then, in a second step, said partial or total surface is subsequently irradiated with UV-visible radiation as previously defined.

In accordance with another variant of the invention, the oxidizing composition is applied to the entire surface of the keratin fibres, then, in a second step, the entire surface is irradiated with UV-visible radiation as previously defined.

According to a third variant of the invention, the oxidizing composition is applied to the entire surface of the keratin fibres, then, in a second step, a part of said surface is irradiated (part of the surface which may be predefined) with UV-visible radiation as previously defined.

Such an embodiment allows the creation of lightened and and/or coloured patterns on the surface of the keratin fibres.

According to another embodiment, the process according to the invention comprises a step of application, to the keratin fibres, of an oxidizing composition and a step of irradiation of said fibres with UV-visible radiation having a wavelength ranging from 200 to 800 nm and a fluence ranging from 1 to 5000 J/$cm^2$, emitted by one or more light-emitting sources, after application of said composition.

Preferably, in this embodiment, the oxidizing composition is aqueous.

Preferentially, the oxidizing agent is hydrogen peroxide.

In accordance with this embodiment, the aqueous oxidizing composition may also comprise one or more basifying agents.

In accordance with these embodiments, the UV-visible radiation has a wavelength ranging from 350 to 450 nm, in particular of 365 nm, 385 nm or 405 nm (±10 nanometers).

According to one embodiment, the process according to the invention is a process for bleaching keratin fibres.

According to one embodiment, the process according to the invention is a process for dyeing keratin fibres.

Preferably, when the process according to the invention with use of a diode is a process for dyeing keratin fibres, the composition containing one or more chemical oxidizing agents also comprises one or more oxidation dyes.

The examples that follow serve to illustrate the invention without, however, being limiting in nature.

In the following examples, the keratin fibres used are hair having a tone level equal to 6 (TL6), which corresponds to a lock of dark blonde hair, or a tone level equal to 4 (TL4), which corresponds to a lock of chestnut brown hair.

The notion of "tone level" is based on the classification of natural shades, one tone separating each shade from the shade immediately following or preceding it. This definition and the classification of natural shades are well known to hairstyling professionals and are published in the book "Sciences des traitements capillaires [Hair treatment science]" by Charles Zviak, 1988, published by Masson, pp. 215 and 278.

The tone levels range from 1 (black) to 10 (very light blond), one unit corresponding to one tone; the higher the figure, the lighter the shade.

EXAMPLES

I. Example 1—Bleaching

In this example, the concentrations of active agents and the treatment time are compared between a bleaching process according to the invention and standard bleaching processes.

A. Compositions Tested

The following oxidizing compositions are prepared, the amounts of which are expressed as percentage by weight of active materials.

|  | Composition A1 |
| --- | --- |
| Hydrogen peroxide | 7.2 A.M |
| Ammonium hydroxide | 0.7 A.M |
| Water | qs 100 |

|  | Composition A2 |
| --- | --- |
| Hydrogen peroxide | 7.2 A.M |
| Potassium persulfate | 6 A.M |
| Ammonium persulfate | 5.9 A.M |
| Water | qs 100 |

B. Light-Emitting Source

The light-emitting source used is a UVA LED bank, Lightnincure LC-L5 365 nm model, sold by Hamamatsu, which is an instrument composed of several light-emitting diodes (LEDs), the wavelength of the light of which is centred on 365 nm.

The instrument is composed of sufficient light-emitting diodes appropriately installed to illuminate a surface area of 60 $cm^2$ with a fluence of between 1 and 5000 J/$cm^2$.

C. Procedure

Each composition (A1) and (A2) is applied to locks of hair which are then irradiated for a period of 15 minutes at a fluence of 676 J/$cm^2$, i.e. under an irradiance of 751 mWatts/$cm^2$. The locks of hair are then rinsed.

The results obtained are compared with those obtained with processes using "Nutrisse ultra éclaircissante" and "Infini Platinium" bleaching compositions according to the modes of use in the instructions therefor.

D. Results

1) Comparison of Active Agent Concentrations

It is noted that the basifying agent content is lower in the compositions according to the invention (A1) and (A2) compared with the "Nutrisse ultra éclaircissante" composition.

In particular, the basifying agent content is 0.7% by weight of active materials in the composition (A1) and is zero in the composition (A2), compared with 3% by weight of active materials in the "Nutrisse ultra éclaircissante" composition.

It is also noted that the persulfate content is lower in the composition (A2) than in the "Infini Platinium" composition, namely 11.9% by weight compared with 35% by weight.

2) Comparison of the Treatment Time

It is noted that a bleaching of 6 tone levels is obtained on TL4 chestnut brown hair with the process according to the invention after 15 minutes of irradiation, whereas an equivalent bleaching is obtained after the composition called "Infini Platinium" has been left in for 50 minutes.

II. Example 2—Bleaching

In this example, the shades obtained are compared between bleaching processes according to the invention and standard bleaching processes.

A. Composition Tested

The composition A1 described in the previous example is used.

B. Light-Emitting Source

The light-emitting source used is a UVA LED bank, Lightnincure LC-L5 365 nm model, sold by Hamamatsu, which is an instrument composed of several UV light-emitting diodes (LEDs), the wavelength of the UV light of which is centred on 365 nm.

The instrument is composed of sufficient light-emitting diodes appropriately installed to illuminate a surface area of 60 cm$^2$ with a fluence of between 1 and 5000 J/cm$^2$.

C. Procedure

1) Process 1

The composition (A1) is applied to locks of chestnut brown hair (TL4) which are then irradiated for a period of 15 minutes at a fluence of 341 J/cm$^2$. The locks of hair are then rinsed.

2) Process 2

The composition (A1) is applied to locks of chestnut brown hair (TL4) which are then irradiated for a period of 15 minutes at a fluence of 460 J/cm$^2$. The locks of hair are then rinsed.

3) Process 3

The composition called "Infini Platinium" is applied to locks of chestnut brown hair (TL4) for a period of 40 minutes. The locks of hair are then rinsed.

4) Process 4

The composition called "Infini Platinium" is applied to locks of chestnut brown hair (TL4) for a period of 50 minutes. The locks of hair are then rinsed.

D. Results—Comparison of the Shades

It is noted that the bleaching processes according to the invention (Processes 1 and 2) result in lightening that adheres more to the natural tone level of the hair without producing a yellow/orangey lightening background.

The table hereinafter gives the lightenings obtained with processes 1 to 4:

The colour of the locks was evaluated in the CIE L* a* b* system, using a Minolta Spectrophotometer CM2600D colorimeter. In this L* a* b* system, the three parameters denote, respectively, the colour intensity (L*), the green/red colour axis (a*) and the blue/yellow colour axis (b*).

In this table, the colorimetric parameters L*, a* and b* are given for untreated locks of hair (TL4) and locks of hair treated with the processes according to the prior art (Processes 3 and 4) and the processes according to the invention (Processes 1 and 2). Furthermore, the values Δa* and Δb* are respectively calculated between a*, once the locks have been bleached, and $a_0$* for the untreated locks, and between b*, once the locks have been bleached, and $b_0$* for the untreated locks.

The table shows that the lightenings obtained with the processes according to the invention are closer to the natural tone level since the components a* and b* vary less significantly than with the processes according to the prior art (Processes 3 and 4) compared with the values of the components a* and b* of chestnut brown hair.

|  | L* | a* | b* | Δa* | Δb* |
|---|---|---|---|---|---|
| TL4 chestnut brown lock (untreated) | 21.1 | 3.08 | 3.14 | — | — |
| Process 3 | 50.34 | 10.56 | 31.4 | 7.48 | 28.26 |
| Process 1 (invention) | 51.42 | 8.4 | 21.19 | 5.32 | 18.05 |
| Process 4 | 54.72 | 11.19 | 30.28 | 8.11 | 27.14 |
| Process 2 (invention) | 54.76 | 7.46 | 19.57 | 4.38 | 16.43 |

III. Example 3—Bleaching

In this example, a bleaching process according to the invention is used which comprises a step of irradiation by means of UV-visible radiation at a wavelength equal to 385 nm and a wavelength at 405 nm at two different fluence ranges.

A. Compositions Tested

The composition A1 described in the previous examples is used.

B. Light Source

B1. Light Source at 385 nm

A UVA LED bank, Lightnincure LC-L5 385 nm model, sold by Hamamatsu, which is an instrument composed of several UV light-emitting diodes (LEDs), the wavelength of the UV light of which is centred on 385 nm, is used.

The instrument is composed of sufficient light-emitting diodes appropriately installed to illuminate a surface area of 60 cm$^2$ with a fluence of between 1 and 5000 J/cm$^2$.

B2. Light Source at 405 nm

A blue LED bank constructed so as to be composed of several UV light-emitting diodes (LEDs), the wavelength of the UV light of which is centred on 405 nm, is used.

The instrument is composed of sufficient light-emitting diodes appropriately installed to illuminate a surface area of 60 cm$^2$ with a fluence of between 1 and 5000 J/cm$^2$.

C. Procedure

C1. Procedure—Light Source at 385 nm

A lock of chestnut brown hair having a TL4 tone level is placed in a drip tray which is intended to then be placed under the UVA LED bank and care is taken to ensure that the lock is correctly located in the irradiation zone.

The UVA LED bank is preheated for a period of one minute.

The composition (A1) is applied to locks of chestnut brown hair having a TL4 tone level, at a rate of 20 grams per 0.5 gram of lock.

The drip tray is placed under the bank, taking care to correctly centre it, and the height of the drip tray relative to the light source is adjusted to a distance of one centimeter (Z=1 cm).

The lock of hair is irradiated at a fluence of 360 J/cm² and a wavelength of 385 nanometers for five minutes, then the lock is turned over in order to irradiate the second side for five minutes. The lock is rinsed and then washed with shampoo.

C2. Procedure—Light Source at 405 nm

A lock of chestnut brown hair having a TL4 tone level is placed in a drip tray which is intended to then be placed under the blue LED bank and care is taken to ensure that the lock is correctly located in the irradiation zone.

The blue LED bank is preheated for a period of one minute.

The composition (A1) is applied to locks of chestnut brown hair having a TL4 tone level, at a rate of 20 grams per 0.5 gram of lock.

The drip tray is placed under the bank, taking care to correctly centre it, and the height of the drip tray relative to the light source is adjusted to a distance of one centimeter (Z=1 cm).

The lock of hair is irradiated at a fluence of 480 J/cm² and a wavelength of 405 nanometers for 20 minutes, then the lock is turned over in order to irradiate the second side for 20 minutes. The lock is rinsed and then washed with shampoo.

C3. Procedure—Light Source at 405 nm

A lock of chestnut brown hair having a TL4 tone level is placed in a drip tray which is intended to then be placed under the blue LED bank and care is taken to ensure that the lock is correctly located in the irradiation zone.

The blue LED bank is preheated for a period of one minute.

The composition (A1) is applied to locks of chestnut brown hair having a TL4 tone level, at a rate of 20 grams per 0.5 gram of lock.

The drip tray is placed under the bank, taking care to correctly centre it, and the height of the drip tray relative to the light source is adjusted to a distance of one centimeter (Z=1 cm).

The lock of hair is irradiated at a fluence of 1440 J/cm² and a wavelength greater than 405 nanometers for 60 minutes, then the lock is turned over in order to irradiate the second side for 60 minutes. The lock is rinsed and then washed with shampoo.

The data from the irradiation steps are indicated hereinafter:

| Apparatus | Irradiance | Fluence | Irradiation Time |
|---|---|---|---|
| 385 nm UVA LED bank (Z = 1 cm) | 1200 mW/cm² | 720 J/cm² | 2 × 5 minutes |
| 405 nm UVA LED bank (Z = 1 cm) | 400 W/cm² | 960 J/cm² | 2 × 20 minutes |
| UVA LED bank greater than 405 nm (Z = 1 cm) | 400 W/cm² | 2880 J/cm² | 2 × 60 minutes |

D. Results—Comparison of the Shades

The colour of the locks was evaluated in the CIE L* a* b* system, using a Minolta Spectrophotometer CM2600D colorimeter. In this L* a* b* system, the three parameters denote, respectively, the colour intensity (L*), the green/red colour axis (a*) and the blue/yellow colour axis (b*).

In this table, the colorimetric parameters L*, a* et b* are given for locks of untreated hair (TL4) and locks of hair treated with the processes according to the invention.

| | L* | a* | b* |
|---|---|---|---|
| TL4 chestnut brown lock (untreated) | 20.12 | 3 | 3.07 |
| Process C1 (385 nm) | 59.54 | 10.4 | 24.25 |
| Process C2 (405 nm) | 50.27 | 10.65 | 22.60 |
| Process C3 (405 nm) | 84.66 | 3.72 | 16.96 |

It is noted that the process according to the invention makes it possible to bleach efficiently at wavelengths of 385 nm and 405 nm at different fluences.

IV. Study of the Light Source

In this example, a process according to the invention is carried out which comprises a step of irradiation performed using a light-emitting source.

B. Compositions Tested

The following oxidizing composition is prepared, the amounts of which are expressed as percentage by weight as it is.

| | Composition A1 |
|---|---|
| Hydrogen peroxide | 7.2 A.M |
| Ammonium hydroxide | 0.7 A.M |
| Water | qs 100 |

B. Light Source

A UVA LED bank, Lightnincure LC-L5 365 nm model, sold by Hamamatsu, is provided as light-emitting source. The instrument is composed of several UV light-emitting diodes (LEDs) emitting UVA rays having a wavelength of 365 nm.

C. Procedure

A lock of dark blonde hair having a TL6 tone level is placed in a drip tray which is intended to then be placed under the UVA LED bank and care is taken to ensure that the lock is correctly located in the irradiation zone.

The UVA LED bank is preheated for a period of one minute.

The composition (A1) is applied to locks of dark blonde hair having a TL6 tone level, at a rate of 20 grams per 0.5 gram of lock.

The drip tray is placed under the bank, taking care to correctly centre it, and the height of the drip tray relative to the light source is adjusted to a distance of six centimeters (Z=6 cm).

The lock of hair is irradiated at a fluence of 36 J/cm² and a wavelength centred around 365 nanometers for two minutes, then the lock is rinsed and washed with shampoo.

D. Results

The colour of the locks was evaluated in the CIE L* a* b* system, using a Data Color SF 600× colorimeter. In this L* a* b* system, the three parameters denote, respectively, the colour intensity (L*), the green/red colour axis (a*) and the blue/yellow colour axis (b*).

In this table hereinafter, the colorimetric parameters L*, a* et b* are given for locks of untreated TL6 hair and locks of hair treated according to the process according to the invention (process C1).

The table also gives the result of the buildup (or variation) of the colouring DE* which was calculated from the values of L*a*b* according to the following equation (i):

$$DE^* = \sqrt{(L^* - L_o^*)^2 + (a^* - a_o^*)^2 + (b^* - b_o^*)^2} \quad (i)$$

In the equation (i), L*, a* and b* represent the values measured on locks of TL6 hair after dyeing according to process C1, and $L_o^*$, $a_o^*$ and $b_o^*$ represent the values measured on locks of undyed TL6 hair. The higher the DE* value, the better the colour buildup or variation.

|  | L* | a* | b* | DE* |
|---|---|---|---|---|
| TL6 lock untreated | 31.46 | 7.44 | 13.26 | — |
| Process C1 | 38.63 | 9.88 | 19.35 | 9.75 |

It is noted that the process according to the invention makes it possible to produce lightening with a significantly short irradiation time.

Consequently, it is noted that the process according to the invention using light-emitting technology is efficient.

V. Dyeing

In this example, a dyeing process according to the invention, comprising a step of application of a composition containing an oxidation base and a coupler in the presence of an oxidizing agent and an irradiation step, is compared with a process comprising a step of application of a composition containing the oxidation base and the coupler and an irradiation step.

A. Compositions Tested

The following dye compositions are prepared, the amounts of which are expressed as percentage by weight of active materials.

|  | Composition B |
|---|---|
| 1-methyl-2,5-diaminobenzene | 0.244 A.M |
| 1,3-dihydroxybenzene | 0.22 A.M |
| Water | qs 100 |

B. Light-Emitting Source

The light-emitting source used is a UVA LED bank, Lightnincure LC-L5 365 nm model, sold by Hamamatsu, which is an instrument composed of several UV light-emitting diodes (LEDs), the wavelength of the UV light of which is centred on 365 nm.

C. Procedure

1) Dyeing Process (in the Absence of Oxidizing Agent)

The composition (B) is applied to locks of natural grey hair containing 90% white hairs, at a rate of 5 grams of composition per 1 gram of lock.

The lock is placed perpendicular to the UVA bank at a distance of 1 cm and a part of the lock is irradiated for a period of 10 minutes at a fluence of 676 J/cm². The entire lock is rinsed and a shampoo is then applied.

2) Dyeing Process According to the Invention

The composition (B) is mixed with an oxidizing composition comprising 20 volumes of hydrogen peroxide (6% of $H_2O_2$) in a 1/1 weight ratio.

The composition resulting from this mixing is applied to locks of natural grey hair containing 90% white hairs, at a rate of 10 grams of composition per 1 gram of lock.

The lock is placed perpendicular to the UVA bank at a distance of 1 cm and a part of the lock is irradiated for a period of 10 minutes at a fluence of 676 J/cm². The entire lock is rinsed and a shampoo is then applied.

D. Results

It is noted that the UVA irradiation promotes coupling with or without oxidizing agent.

The invention claimed is:

1. A process for bleaching or dyeing keratin fibers, the process comprising:
   (i) a step of application, to said fibers, of a composition containing one or more chemical oxidizing agents,
   (ii) a step of irradiation of said fibers by UV-visible radiation having a wavelength ranging from about 200 nm to about 800 nm and a fluence ranging from about 1 J/cm² to about 5000 J/cm², after application of said corn position;
   (iii) when the process is a process for dyeing keratin fibers, then said process also uses one or more oxidation dyes.

2. The process according to claim 1, wherein the irradiation step is carried out by one or more light sources.

3. The process according to claim 1, wherein the irradiation step is carried out by one or more light-emitting sources chosen from light-emitting diodes (LEDs) or organic light-emitting diodes (OLEDs).

4. The process according to claim 1, wherein the keratin fibers, once treated with the oxidizing composition, are irradiated for a period of less than about 60 minutes.

5. The process according to claim 1, wherein the chemical oxidizing agent(s) are chosen from hydrogen peroxide and/or persalts.

6. The process according to claim 1, wherein the oxidation dyes are chosen from oxidation bases and optionally couplers.

7. The process according to claim 6, wherein the oxidation bases are chosen from para-phenylenediamines, bis(phenyl) alkylenediamines, para-aminophenols, ortho-aminophenols and heterocyclic bases, 2-methoxymethyl-para-phenylenediamine, 2-β-hydroxyethyl-para-phenylenediamine, la N,N-bis-(β-hydroxyethyl)-para-phenylenediamine, 1-methyl-2,5-diaminobenzene, para-aminophenol, 1-hydroxyethyl-4,5-diaminopyrazole, 2,3-diaminodihydroxypyrazolone dimethosulfonate, 2-(2-hydroxyéthoxy)-3-amino pyrazolo[1,5-a]pyridine, the addition salts thereof, or mixtures thereof.

8. The process according to claim 6, wherein the couplers are chosen from meta-phenylenediamines, meta-aminophenols, meta-diphenols, naphthalene-based couplers and heterocyclic couplers, resorcinol, 2-methylresorcinol, 5-amino-6-chloro-2-methylphenol, 2-amino-4-(β-hydroxyethylamino)-1-methoxybenzene, 5-N-(β-hydroxyethyl)amino-2-methylphenol, 2-methyl-5-aminophenol, 1-β-hydroxyethyloxy-2,4-diaminobenzene hydrochloride and 3-aminophenol, the addition salts thereof, or mixtures thereof.

9. The process according to claim 1, wherein the composition also contains one or more basifying agents.

10. The process according to claim 9, wherein the basifying agent is chosen from aqueous ammonia, organic amines, inorganic bases, or mixtures thereof.

11. The process according to claim 1, wherein the composition does not exhibit an absorption peak in the range of wavelengths used for the irradiation step.

12. The process according to claim 1, wherein the UV-visible radiation has a wavelength ranging from about 350 nm to about 450 nm.

13. The process according to claim 1, wherein the UV-visible radiation has a fluence ranging from about 50 J/cm$^2$ to about 2000 J/cm$^2$.

14. The process according to claim 1, wherein the composition is rinsed out after the keratin fiber irradiation step.

15. A process for bleaching or dyeing keratin fibers, in particular human keratin fibers, comprising:
- (i) a step of application, to said fibers, of a composition comprising one or more chemical oxidizing agents,
- (ii) a step of irradiation of the keratin fibers by one or more diodes chosen from light-emitting diodes (LEDs) or organic light-emitting diodes (OLEDs) after application of said composition, when the process is a process for dyeing keratin fibers, then said process also uses one or more oxidation dyes.

* * * * *